United States Patent
Collins et al.

(10) Patent No.: US 6,821,431 B2
(45) Date of Patent: Nov. 23, 2004

(54) IONIC ENHANCED DIALYSIS/ DIAFILTRATION SYSTEM

(75) Inventors: Gregory R. Collins, Monroe, NY (US); James Summerton, Hillsdale, NJ (US); Edward Spence, Bronx, NY (US)

(73) Assignee: Nephros, Inc., New York, NY (US)

( * ) Notice: Subject to any disclaimer, the term of this patent is extended or adjusted under 35 U.S.C. 154(b) by 143 days.

(21) Appl. No.: 10/181,138

(22) PCT Filed: Jan. 11, 2001

(86) PCT No.: PCT/US01/01023
§ 371 (c)(1),
(2), (4) Date: Jul. 9, 2002

(87) PCT Pub. No.: WO01/51184
PCT Pub. Date: Jul. 19, 2001

(65) Prior Publication Data
US 2003/0010701 A1 Jan. 16, 2003

Related U.S. Application Data
(60) Provisional application No. 60/175,578, filed on Jan. 11, 2000.

(51) Int. Cl.[7] .................. B01D 61/24; B01D 61/26; B01D 61/28
(52) U.S. Cl. .......... 210/646; 210/257.2; 210/321.6; 210/321.71; 210/321.72; 210/433.1; 210/645; 210/647
(58) Field of Search ............... 210/85, 87, 194, 210/195.2, 257.2, 321.6, 321.71, 321.72, 321.84, 433.1, 434, 645, 646, 647, 739, 805; 422/44; 604/4.01, 5.01

(56) References Cited

U.S. PATENT DOCUMENTS

| | | | | |
|---|---|---|---|---|
| 5,660,722 A | * | 8/1997 | Nederlof | 210/90 |
| 5,744,042 A | * | 4/1998 | Stange et al. | 210/645 |
| 6,406,631 B1 | * | 6/2002 | Collins et al. | 210/646 |
| 6,526,357 B1 | * | 2/2003 | Soussan et al. | 702/45 |

* cited by examiner

Primary Examiner—John Kim
(74) Attorney, Agent, or Firm—Darby & Darby

(57) ABSTRACT

A dual-stage system and methods for using the same include first and second filtration cartridges is provided and is particularly suited for hemodiafiltration and/or hemodialysis. As fluid enters the first diafiltration cartridge, the hydrogenion concentration (pH) is reduced by exposing it to an acidic solution such as citric acid across a filter membrane. This stage allows for improved removal of certain toxins in the fluid, such as protein-bound substances that disassociate more readily from proteins at lower pH. As the filtered fluid enters the second filtration cartridge, the pH of the fluid is restored to normal levels prior to infusion to a patient.

27 Claims, 2 Drawing Sheets

IONIC ENHANCED DIALYSIS/DIAFILTRATION SYSTEM

CROSS-REFERENCE TO RELATED APPLICATIONS

This application is a U.S. national phase application under 35 U.S.C. §371 based upon co-pending International Application No. PCT/US01/01023 filed Jan. 11, 2001, which claims the benefit of priority of U.S. Provisional Application Ser. No. 60/175,578 filed Jan. 11, 2000. The entire disclosure of the prior applications are incorporated herein by reference. The international application was published in the English language on Jul. 19, 2001 under Publication No. WO 01/51184.

FIELD OF THE INVENTION

This invention relates to dialysis and hemodiafiltration in general and, more particularly, to improved hemodiafiltration methods and devices for removal of blood toxins.

BACKGROUND OF THE INVENTION

Hemodialysis and Hemodiafiltration are well known methods for removing toxic substances from a patient's blood, thereby reducing the level of toxins in the patient's blood as part of an extracorporeal blood cleansing system. Both these methods are based on flowing blood through a cartridge containing a semi-permeable membrane which separates the cartridge into two compartments. In general, hemodialysis is a process whereby blood flows through a blood-side compartment of the cartridge, while a cleansing solution, i.e., a dialysate solution, flows through a dialysate-side compartment of the cartridge. Toxins are removed from the blood by diffusion across the semi-permeable membrane from the blood-side compartment to the dialysate-side compartment. The rate of diffusion is determined by the concentration gradient established between a higher concentration of toxins in the blood relative to the dialysate fluid. Hemodiafiltration is process whereby the normal removal of toxins by diffusion is augmented by a convective flow of plasma water across the semi-permeable membrane which assists in carrying toxins by bulk flow of fluid from the bloodside of the membrane to the dialysate side of the membrane. The transportation of plasma water across the semi-permeable membrane is achieved by establishing a pressure gradient, generally referred to as Transmembrane Pressure (TMP), across the membrane. In hemodiafiltration, an equivalent amount of a substitution fluid, or replacement fluid, must be added to the blood to replace the plasma water that is filtered across the membrane. This substitution fluid is generally added either before the blood enters the cartridge (pre-dilution mode) or after the blood exits the cartridge (post-dilution mode).

Hemodiafiltration systems using two cartridges connected in series are also known in the art. In such systems, a first cartridge is used as a conventional diafiltration cartridge providing simultaneous diffusion and filtration of plasma water across the semi-permeable membrane. In a second cartridge, toxins are diffused from the blood to the dialysate fluid, and a reverse pressure gradient is used to reverse-filter dialysate fluid from the dialysate-side compartment, across the membrane, and into the blood-side compartment. The reverse-filtered dialysate fluid serves as a substitution fluid to replace the amount of plasma water that is filtered from the blood-side compartment to the dialysate-side compartment in the first cartridge. Such a method is described in J. H. Miller et al., "Technical Aspects of High-Flux Hemodiafiltration for Adequate Short (Under 2 Hours) Treatment," Transactions of American Society of Artificial Internal Organs (1984), pp. 377–380.

SUMMARY OF THE INVENTION

Certain hemodialysis/diafiltration applications use two cartridges connected in series. The dialysate fluid in the first cartridge is made hypertonic or hypotonic (by adjusting the electrolyte levels of the dialysate stream) to improve toxin removal efficiency. This method is disclosed in PCT Application No. PCT/US99/25804 entitled "Non-Isosmotic Diafiltration System" filed in the name of Collins et al., the entirety of which is hereby incorporated by reference.

One embodiment of the present invention includes a method whereby hydrogen ion concentration (or pH) of the dialysate fluid entering a first filtration cartridge is reduced by introducing a secondary acid solution. The second filtration cartridge then serves to correct for blood pH shifts occurring in the first filtration cartridge. One advantage of this method is that it allows one to carry out the diffusion and/or diafiltration process in the first cartridge outside the normal limit of blood pH. This method improves the removal of certain substances, such as protein-bound substances that disassociate more readily from proteins at low pH. This method also allows for enhanced removal of other substances that may be affected by changes in the number of charged polar groups (acidic or basic) and/or structural changes of blood proteins (i.e., those proteins circulating in the blood stream or those protein that accumulate and/or adsorb near the semi-permeable membrane) due to changes in pH.

An additional benefit is possible when the acid that is used in the dialysate stream of the first cartridge is citric acid. In this case, the ionized citrate molecule can diffuse into the blood compartment of the first cartridge where it binds to ionized calcium. This has the potential effect of reducing the amount of clotting in the cartridges as citrate has certain anti-coagulation properties. Ionized calcium is replaced in the blood stream by back diffusion and/or back filtration of calcium from the standard dialysate that passes through the second cartridge. If substitution fluid is introduced between the two cartridges as described above, this also acts as a source of calcium for the blood stream.

It is a further object of the invention to provide hemodialysis or hemodiafiltration method using two cartridges (or two stages), preferably in series, that improves clearance of certain substances by introducing an acidic solution into the dialysate fluid stream of the first cartridge. The process is such that blood in the first cartridge is dialyzed or diafiltered against a low pH dialysate solution, while blood in the second cartridge is dialyzed or diafiltered against a standard dialysate (i.e., within a pH range from 7.0 to 7.8). The second cartridge then may serve three main functions which are 1) to correct for blood pH shifts caused by the low pH dialysate in the first cartridge, 2) to continue to remove blood toxins by diffusion or diafiltration against standard dialysate, and 3) to correct for electrolyte imbalances in the blood. In a hemodialysis application, correction of blood pH and electrolyte imbalance is accomplished by diffusion of neutralizing substances (such as bicarbonate) and electrolytes across the semi-permeable membrane separating the blood and dialysate compartments of the second cartridge. In a hemodiafiltration application, these corrections are accomplished by introducing a substitution fluid containing neutralizing substances (such as bicarbonate) and electrolytes into the blood stream in addition to diffusion across the semi-permeable membrane of the second cartridge.

The present invention may be embodied in an improved dialysis machine that allows for the addition of a secondary acid solution into the dialysate fluid path. The machine may include other basic components used in current dialysis machines, such as a water preparation module to degas and heat water necessary for preparing dialysate, an ultrafiltration control system which may include a flow balancing system and an ultrafiltration (UF) pump, a dialysate proportioning system which may introduce dialysate concentrates into the water stream, and extracorporeal monitoring and control components which may include a blood pump for circulating blood through the extracorporeal circuit.

When performing hemodiafiltration, a system of the present invention may include a substitution fluid system (including pump and substitution fluid filters when preparing a substitution fluid on-line using dialysate fluid), and an interdialysate flow control system (which may include an interdialysate pump) to regulate the relative ultrafiltration rates of the two dialyzer cartridges.

In a preferred embodiment, blood to be cleansed flows into a first dialyzer or diafilter cartridge. The cartridge contains a semi-permeable membrane that separates the cartridge into two compartments, a first compartment containing the blood to be cleansed, and a second compartment containing a dialysate fluid. The pH of the dialysate fluid in this compartment is reduced below that of standard dialysate (i.e., pH<7.0) by addition of a second acid stream (such as citric acid) before the dialysate is delivered to this first dialyzer cartridge. The effect of this is to decrease the pH of the blood in order to enhance removal of certain substances. These substances might include protein-bound substances that may dissociate at lower pH conditions or other substances that may be affected by changes in the number of charged polar groups (acidic or basic) of proteins in the blood stream. For the special case of using citric acid, the effect may also include a decrease in blood clotting in the extracorporeal circuit due to the anti-coagulation properties of citrate.

As blood flows through the blood compartment of the first dialyzer cartridge, in addition to the pH of the blood being lowered, toxins are removed by diffusion resulting from a concentration gradient between the blood and the dialysate fluid. Also, electrolytes may be imbalanced depending on the amount of dilution that may or may not occur as a result of adding the acid stream to the dialysate fluid. If performing diafiltration, an additional removal of toxins may occur by convection as a portion of plasma water from the blood compartment is filtered across the semi-permeable membrane and into the dialysate compartment.

Upon exiting the first dialyzer cartridge, the partially dialyzed/diafiltered blood may be mixed with a substitution fluid. The substitution fluid helps correct the pH shift and electrolyte imbalance resulting from the first cartridge process since the substitution fluid contains necessary neutralizing agents, such as a bicarbonate, and proper electrolyte levels.

The blood then enters a second dialyzer cartridge. In this second cartridge, the blood is dialyzed (or diafiltered) against a standard dialysate containing electrolytes within their normal ranges. Blood toxins continue to move across the semi-permeable membrane into the dialysate fluid by diffusion (and perhaps by convection), while electrolytes and neutralizing agents from the dialysate may move across the semi-permeable membrane and into the blood. Upon existing the second cartridge, the blood pH and composition of electrolytes are within normal ranges.

Dialysate fluid is prepared by proportioning dialysate concentrates with a treated water as is known in the art. Flow of the dialysates fluid into and out of the dialyzer cartridges is controlled precisely using a flow balance system that is known in the art. In treating a patient according to the present invention, the device typically must remove a portion of plasma water in order to maintain the patient's dry weight. This can be done using an ultrafiltration pump as is known in the art. When performing diafiltration, substitution fluid may be generated on line using a portion of the fresh dialysate fluid by filtering it through at least one sterilizing filter or substitution fluid filter.

Fresh dialysate enters into the dialysate inlet of the second cartridge, where it may flow countercurrent to the blood flow. As the dialysate fluid traverses the cartridge, toxins and ultrafiltered plasma water from the blood begin to accumulate in the dialysate fluid. Some electrolytes and neutralizing agents from the dialysate may be depleted from the dialysate fluid as they move from the higher concentration in the dialysate to the lower concentration in the blood.

The partially spent dialysate fluid exiting the dialysate outlet of the second cartridge is mixed in a mixing chamber with a metered portion of an acid solution (preferably a citric acid solution) to reduce the dialysate pH to below 7.0. In one embodiment, the acid solution source is a saturated solution obtained by flowing a portion of treated water through a closed container containing the powdered form of dry acid. In a second embodiment, the acid solution is introduced from an externally supplied container using a pump. The mixed dialysate stream then flows toward the dialysate inlet of the first cartridge. A regulator which controls the relative amounts of plasma water filtered off in the two cartridges may be used. For example, a servo- controlled interdialysate pump that changes speed based on an algorithm calculated using measured pressure differentials (TMP's) across the semi-permeable membrane may be used.

The partially spent acidic dialysate fluid then enters the dialysate inlet of the first cartridge. As it flows through the cartridge, blood toxins and filtered plasma water may accumulate in this fluid. The low pH of this dialysate fluid results in an imbalance of hydrogen ions across the membrane such that the pH of the blood may decrease below its normal range. In the preferred example using citric acid, additional anticoagulation properties may be gained due to the inherent properties of citrate as an anticoagulant. The spent dialysate fluid exits the first cartridge and flows back toward the flow balance system where it eventually flows out to the drain.

It should be apparent to those skilled in the art that this method can be performed with at least two dialyzer cartridges operation in a typical dialysis mode or it can be performed with two high flux dialyzer or diafiltration cartridges is a hemodiafiltration mode. The limiting factor being the ability of the second cartridge to recover from the perturbation caused by the first cartridge. A preferred method includes the diafiltration mode whereby the substitution fluid is introduced into the blood stream between the two cartridges, so as to help restore the blood back to its normal ranges prior to infusion to a patient.

BRIEF DESCRIPTION OF THE DRAWINGS

Further aspects of the instant invention will be more readily appreciated upon review of the detailed description of the preferred embodiments included below when taken in conjunction with the accompanying drawings, of which.

DETAILED DESCRIPTION OF THE INVENTION

Figure 1:
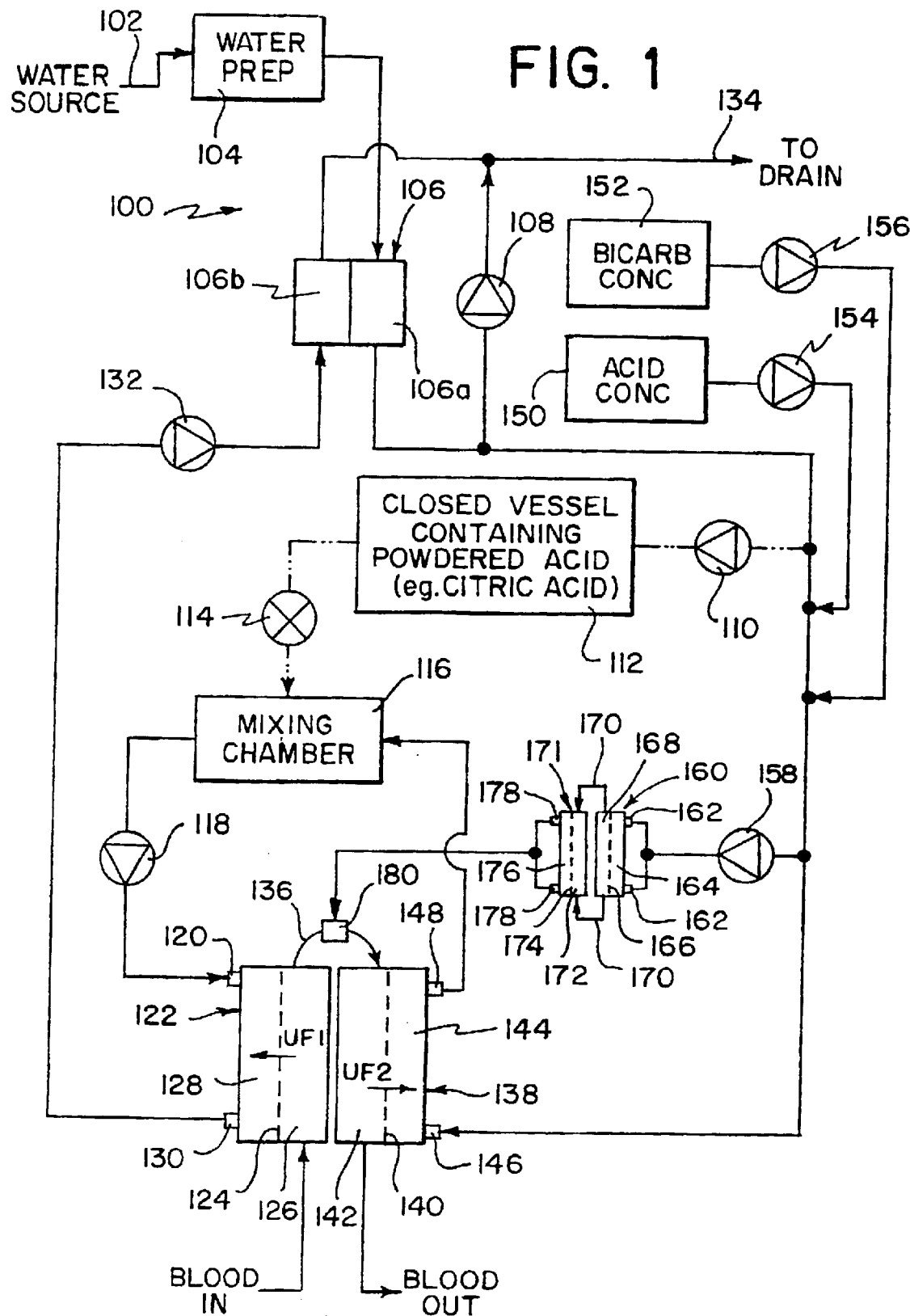
FIG. 1 is a schematic diagram illustrating a first embodiment of a multistage hemodiafiltration device using an internally supplied acid stream.
Figure 2:
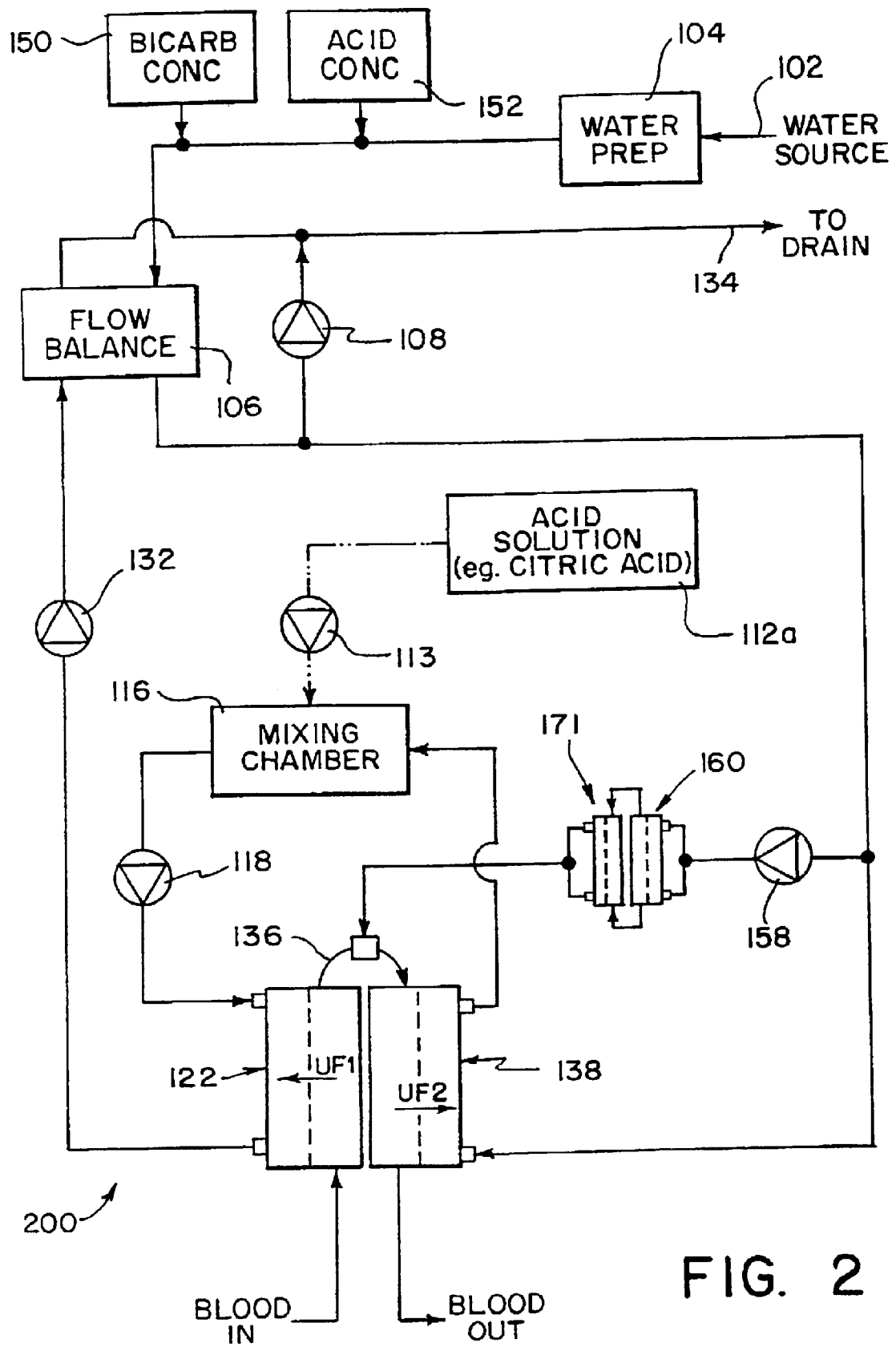
FIG. 2 is a schematic diagram illustrating a first embodiment of a multistage hemodiafiltration device using an externally supplied acid stream.

Referring now to FIGS. 1–2, wherein similar components of the instant invention are referenced in like manner, a preferred apparatus for ionic enhanced dialysis/diafiltration, and accompanying methods for using the same, are disclosed.

Turning now to FIG. 1, depicted therein is a first embodiment of a hemodialysis/diafiltration device which uses an internally supplied acid solution stream.

A water source 102 supplies water or other base fluids, such as saline, to system 100 in order to create dialysate, substitution fluids and the like. The water, or other fluid is then provided to a water preparation device 104 which pre-treats the incoming fluid by heating, degassing and/or any other suitable method known to one of ordinary skill in the art.

The pre-treated fluid is next transported via appropriate tubing or the like to a flow balance system 106 which has an inlet controller 106a and outlet controller 106b, which in turn may continuously monitor and adjust flow rates of fluids entering or exiting the internal components of system 100. Flow balance system 106 may contain one or more microprocessor controls and the like which are programmed to automatically accomplish this functionality within pre-defined parameters.

The pre-treated fluid is transported first to internal components of system 100 through inlet controller 106a. A portion of the pre-treated fluid equivalent to the net amount of fluid to be removed from the patient may be siphoned through an ultrafiltration pump 108 to a drain 134. A remaining portion of pre-treatment fluid is next transported via appropriate tubing or the like to an auxiliary pump 110.

Pump 110 transports a pre-determined portion of the pre-treated fluid to a closed vessel 112 which may contain concentrated acid, such as citric acid or the like, to form a secondary acidic solution for provision to dialyzer cartridge 122, as described below. Pump 110 may be controlled by, for example, a microprocessor controller which is programmed to accept a predetermined portion of pre-treated fluid for creating the secondary acidic solution. Alternatively, the flow through pump 110 may be manually monitored and adjusted as needed.

The secondary acidic solution flows from vessel 112 to an acid inlet valve 114. The acid inlet valve may likewise be automatically or manually controlled to allow a predetermined rate of secondary acidic solution to flow therethrough. The secondary acidic solution then flows to a mixing chamber 116. The mixing chamber 116 has a second inlet which receives dialysate solution from outlet port 148 of second dialyzer cartridge 138, described further below. Mixing chamber 116 may be automatically or manually monitored and adjusted to allow a predetermined amount of secondary acidic solution to flow to inlet port 120 of first dialyzer cartridge 122 via interdialysate pump 118.

A remaining portion of the pre-treated fluid which is not accepted through pump 110 is transported to inlet port 146 of second dialyzer cartridge 138. The system 100 may be provided with monitoring means for determining the appropriate pH that is required to return blood treated in first dialyzer cartridge 122 to a normal level. Once that level has been determined, the acid pump 154 and/or a bicarbonate pump 156 may be employed to pull additional acid concentrate 150 or bicarbonate concentrate 152 to adjust the pH of the remaining pre-treated fluid prior to providing the fluid to inlet 146.

Blood to be cleaned is received from a patient and enters the first dialyzer cartridge 122. The blood is carried by suitable tubing, as is known in the art, for example, blood-line tubing made from flexible polyvinylchloride (PVC). The flow rate of incoming blood is generally in the range of 100 to 600 ml/min, preferably 200 to 500 ml/min. First dialyzer cartridge 122 contains a semi-permeable membrane 124 that divides the dialyzer cartridge 122 into a bloodside compartment 126 and a dialysate compartment 128. As blood passes through blood compartment 126, plasma water containing blood substances is filtered across semi-permeable membrane 124. At the same time, acidic dialysate received from dialysate port 120 flows through dialysate compartment 128 in a direction counter to the blood flow. Blood substances and toxins are transferred across semi-permeable membrane 124 by diffusion due to a difference in concentration between the blood in blood compartment 126 and the acidic dialysate in dialysate compartment 128. The acidic dialysate containing blood substances and toxins removed from the blood are transported to drain 134 via dialysate pump 132 and outlet controller 106b.

The partially dialyzed blood then exits first dialyzer cartridge 122 through conduit 136. The blood then flows through conduit 136 and enters bloodside compartment 142 of second dialyzer cartridge 138. The second dialyzer cartridge preferably contains a semi-permeable membrane 140 which divides the second dialyzer cartridge 138 into a bloodside compartment 142 and a dialysate compartment 144. As the blood passes through bloodside compartment 142, plasma water containing blood substances is filtered across the semi-permeable membrane 140. The pH of the treated blood is returned to a desired concentration due to the difference in pH concentration between the low pH blood in bloodside compartment 142 and the higher pH dialysate in dialysate compartment 144 as received through inlet port 146. Cleansed blood then exits the second dialyzer cartridge 138 and is recycled to the patient (not shown) through suitable tubing, for example, bloodline PVC tubing, as is known in the art. The dialysate exits the dialysate compartment 144 of second dialyzer cartridge 138 through outlet port 148 and is provided to mixing chamber 116, described above.

The dialyzer cartridges 122, 138 may be of any type suitable for hemodialysis, hemodiafiltration, hemofiltration, or hemoconcentration, for example, the Fresenius F60, available from Fresenius Medical Care, Lexington, Mass., the Baxter Conn. 110, available from Baxter Health Care, Deerfield, Ill., the Minntech Hemocor HPH 400, available from Minntech Corporation, Minneapolis, Minn., or the Hospal Filtral 16, available from Hospal A. G., Switzerland. Membranes 124, 140 are preferably medium or high flux membranes, for example, the polysulfone, cellulose triacetate or acrylonitrile membranes available from Fresenius Medical Care, Lexington, Mass., Minntech Corporation, Minneapolis, Minn., Baxter Health Care, Deerfield, Ill., or Hospal A. G., Switzerland.

In an embodiment of the present invention in which diafiltration is desired, the blood may be mixed with sterile substitution fluid between the first and second dialyzer cartridges at inlet 180 of conduit 136 to form a blood/substitution fluid mixture. One way to accomplish this is disclosed in PCT Application No. PCT/US99/17468 entitled "Method for Efficient Diafiltration" filed in the name of Collins et al., the entirety of which is hereby incorporated by reference. Collins et al. uses two cartridges connected in series to perform forward filtration of plasma water from the blood compartment to the dialysate compartment in both cartridges simultaneously. Substitution fluid is added directly into the blood after it exits the first cartridge and before it enters the second cartridge.

In the present invention, preparation of a sterile substitution fluid may be performed by filtration of a portion of pre-treated dialysate which is received from the inlet controller 106a through substitution filter pump 158. The pre-treated dialysate flows across at least two filter membranes 166, 174 with a preferred molecular weight cut-off of not more than 40,000 Daltons. To accomplish this, a portion of the fresh dialysate solution may be split off the dialysate fluid stream at some point prior to entering dialysate compartment 144 of the second dialyzer cartridge 138. The split-off portion of the dialysate solution may flow through a conduit or the like which leads to a substitution pump 158. Substitution fluid pump 158 generates the needed pressure to force the fluid down a conduit into inlet ports 162 of first substitution fluid filter cartridge 160.

First substitution filter cartridge 160 contains a semi-permeable membrane 166 that separates the filter cartridge 160 into an upstream compartment 164 and a downstream compartment 166. First upstream compartment 164 has inlet ports 162. First downstream compartment 168 has one or more outlet ports connected to conduits 170. The substitution fluid from first downstream compartment 168 then flows into second substitution fluid cartridge 171 containing a semi-permeable membrane 174 which separates the second cartridge 171 into a second upstream compartment 172 and a second downstream compartment 176. The sterile substitution fluid exits second substitution fluid cartridge 171 through second outlet ports 178 and is mixed with blood exiting first cartridge 122 to form the blood/substitution fluid mixture described above.

The pre-treated dialysate not used as substitution fluid enters the second dialyzer cartridge 138 through inlet port 146 of dialysate compartment 144, and flows counter-parallel to the blood flow as it traverses through bloodside compartment 142. During diafiltration, excess plasma water filters across semi-permeable membrane 140 and mixes with the dialysate fluid, so as to maintain a patient's dry weight as the treated blood is infused. The dialysate fluid together with the filtered plasma water exits the second dialyzer cartridge 138 at outlet port 148, through a tube or conduit which directs the fluid to the mixing chamber 116, described previously above.

Referring now to FIG. 2, therein is depicted second embodiment of a hemodialysis/diafiltration system 200 which uses an externally supplied acid solution stream. The system 200 functions in a similar manner to system 100 except that acid solution 112a may be provided pre-mixed from an external source, and drawn into the mixing chamber 116 by an acid pump 113, rather than being mixed within the machine as in system 100.

The dialysis/diafiltration methods and devices of present invention described above may be used as an add-on type system in conjunction with an existing ultrafiltration-controlled dialysis machine. However, it should be appreciated that the dialysis/diafiltration methods and devices of the present invention can also be embodied in a unitary, stand-alone dialysis/diafiltration machine.

In one embodiment of the present invention, the dialysis/diafiltration device includes first and second dialyzer cartridges 122, 138. Alternatively, a single cartridge having at first and second separate dialyzer sections may be used.

The device may also include at least one sterility filter 160, 171, which may contain semi-permeable membranes. The sterility filter(s) 160, 171 are operative to remove bacteria, endotoxins, and other particulate from the dialysate, thereby generating a suitable substitution fluid stream on-line. A sterile/non-pyrogenic substitution fluid for use in conjunction with the present invention may be prepared by drawing a portion of fresh dialysate solution from a dialysate inlet line and pumping it through one or more sterile filter cartridge 160, 171. In a preferred embodiment of the present invention, the sterile filter cartridges 160, 171 perform at least a double filtration of the dialysate solution before the solution is introduced into the blood as a substitution fluid. This double filtration can be performed by two separate ultrafiltration filter cartridges or a single cartridge that has multiple sections to perform multiple filtration of the substitution fluid. The use of multiple filtration to generate the on-line substitution fluid makes the system of the present invention safer, should one of the filters fail during treatment.

During operation of one embodiment of the present invention, blood enters a blood side compartment 126 of a first dialyzer cartridge 122, whereby a portion of plasma water is filtered across the semi-permeable membrane 124 into the adjacent dialysate compartment 128. As the blood leaves the first dialyzer cartridge 122, substitution fluid may be added to the blood at a rate higher than the rate at which blood is filtered out of the first dialyzer cartridge. The diluted blood may then enter the bloodside compartment 142 of the second dialyzer cartridge 138, whereby additional plasma water (equal to the excess amount of substitution fluid) is filtered across the semi-permeable membrane 140 and into the adjacent dialysate compartment 144. In this manner, the substitution fluid acts as a post-dilution fluid relative to the first dialyzer cartridge as well as a pre-dilution fluid relative to the second dialyzer cartridge.

The dialysate fluid may be generated by a dialysis machine, or by any other method known to one of ordinary skill in the art. In an embodiment of the present invention, the dialysate fluid enters the second dialyzer cartridge 138 and runs counter-parallel to the blood flow direction. The dialysate fluid acts to provide a concentration gradient against the bloodside fluid thereby facilitating the diffusion of solutes across the semi-permeable membrane 140. As the dialysate traverses through the dialysate compartment, the dialysate flow rate increases due to plasma water filtering across into the dialysate compartment 144, as mentioned above. Upon exiting the second dialyzer cartridge 138, the dialysate fluid may be pumped into the mixing chamber 116. Upon exiting the dialyzer cartridges 122, 138, the used dialysate may be transported back either to the dialysis machine or to the drain 134.

The dialysis machine (riot shown) used in conjunction with the present invention may perform all of its normal functions, such as preparing dialysate, metering dialysate flow rate, monitoring pressures, controlling net ultrafiltration, monitoring used dialysate for blood presence, etc. The diafiltration add-on system operates in conjunction with the dialysis machine, whereby the dialysate fluid from the dialysis machine is re-distributed by the hemodiafiltration add-on system to its respective dialyzer and sterile filter cartridges. The fluid handling components of the diafiltration add-on system may be integrated with a microprocessor unit for controlling and executing the diafiltration aspect of the treatment.

The systems disclosed in the foregoing may contain further pumps, monitoring devices, valves, electronic components, controllers, connector fittings, tubing, etc., as required in order to coordinate the operation of the system components.

Although the invention has been described in detail in the foregoing embodiments, it is to be understood that they have been provided for purposes of illustration only and that other variations both in form and detail can be made thereupon by those skilled in the art without departing from the spirit and scope of the invention, which is defined solely by the appended claims.

We claim:

1. In a blood dialysis system including a source of substitution fluid and a blood dialysis machine, a hemodiafiltration device comprising:

a source of a first dialysate fluid having a first pH and a source of a second dialysate fluid having a second pH;

a first dialyzer including:
a first semi-permeable membrane partitioning said first dialyzer into:
a first blood compartment having a first blood inlet which receives blood to be cleaned and a first blood outlet which expels partially diafiltered blood; and
a first dialysate compartment having a first dialysate inlet connected to said source of the first dialysate fluid and a first dialysate outlet, said first dialysate inlet for accepting said first dialysate fluid having a first pH;

a chamber for mixing said partially diafiltered blood with substitution fluid from said source to obtain a blood/substitution fluid mixture; and a second dialyzer including:
a second semi-permeable membrane partitioning said second dialyzer into:
a second blood compartment having a second blood inlet which receives said blood/substitution fluid mixture and a second blood outlet which expels diafiltered blood; and
a second dialysate compartment having a second dialysate inlet connected to said source of the second dialysate fluid and a second dialysate outlet, said second dialysate inlet for accepting a second dialysate fluid having a second pH, said first pH of said first dialysate fluid being less than said second pH of said second dialysate fluid.

2. A device according to claim 1, wherein said first pH of said first dialysate fluid is less than a pH of said blood in said first blood compartment, said second pH of said second dialysate fluid being greater than a pH of said blood/substitution fluid mixture.

3. A device according to claim 1, further comprising:

a source of second dialysate fluid, said first dialysate fluid comprising a portion of said second dialysate fluid from said source which is treated with a pH modifying agent which reduces the pH of said second dialysate to form said first dialysate fluid.

4. A device according to claim 3, wherein said pH modifying agent is a concentrated acid.

5. A device according to claim 3, wherein said pH modifying agent is citric acid.

6. A device according to claim 3, wherein said first dialysate fluid is formed by diverting said portion of said second dialysate fluid to a container holding said pH modifying agent, whereby the pH of said second dialysate fluid is decreased due to contact with said pH modifying agent to form said first dialysate fluid.

7. A device according to claim 1, further comprising:

a mixing chamber for receiving an acid solution comprising a portion of said second dialysate fluid treated with a concentrated acid, said mixing chamber receiving said second dialysate fluid from said second dialysate outlet so that said acidic solution and said second dialysate fluid are mixed to form said first dialysate fluid.

8. A device according to claim 1, wherein said first dialysate outlet is connected to a drain so that said first dialysate fluid flows through said first dialysate outlet to said drain after flowing through said first dialysate compartment.

9. A device according to claim 1, wherein said first pH is less than about 7.0.

10. A device according to claim 1, wherein said second pH is greater than about 7.0.

11. A device according to claim 1, wherein said second pH is greater than about 7.0 but less than about 7.8.

12. A device according to claim 1, wherein a pH of said blood in said first dialyzer is less than a pH of said blood/substitution fluid mixture due to said blood in said first dialyzer being in diffusion communication with said first dialysate.

13. A blood cleansing system comprising:

a source of a first dialysate fluid having a first pH and a source of a second dialysate fluid having a second pH:

a first dialyzer including:
a first semi-permeable membrane partitioning said first dialyzer into:
a first blood compartment having a first blood inlet which receives blood to be cleaned and a first blood outlet which expels partially cleansed blood; and
a first dialysate compartment having a first dialysate inlet connected to said source of the first dialysate fluid and a first dialysate outlet, said first dialysate inlet for accepting a first dialysate fluid having a first pH; and a second dialyzer including:
a second semi-permeable membrane partitioning said second dialyzer into:
a second blood compartment having a second blood inlet which receives said partially cleansed blood and a second blood outlet which expels cleaned blood; and
a second dialysate compartment having a second dialysate inlet connected to said source of the second dialysate fluid and a second dialysate outlet, said second dialysate inlet for accepting a second dialysate fluid having a second pH, said first pH of said first dialysate fluid being less than said second pH of said second dialysate fluid.

14. A system according to claim 13, further comprising:

a source of substitution fluid, said substitution fluid being mixed with said partially cleansed blood to form a blood/substitution fluid mixture which is delivered to said second blood inlet, said second pH being higher than a pH of said blood/substitution fluid mixture and said first pH being less than a pH of said blood in said first dialyzer.

15. A system according to claim 14, wherein said blood undergoes diafiltration in said first dialyzer and said blood/substitution fluid mixture undergoes diafiltration in said second dialyzer.

16. A system according to claim 14, wherein said second dialysate fluid flows from said second dialysate outlet to a chamber where said pH of said second dialysate fluid is decreased from said second pH to said first pH to form said first dialysate fluid, said first dialysate fluid being delivered to said first dialysate inlet.

17. A method of cleansing blood comprising:

supplying a blood inflow;

dialyzing said blood inflow in a first dialyzer to provide partially dialyzed blood, said first dialyzer receiving a first dialysate fluid having a first pH; and dialyzing said partially dialyzed blood in a second dialyzer, said second dialyzer receiving a second dialysate having a second pH, said first pH being less than said second pH.

18. A method according to claim 17, wherein said first pH is less than a pH of said blood inflow and said second pH is greater than a pH of said partially dialyzed blood.

19. A method according to claim 17, wherein a pH of said blood inflow is substantially equal to a pH of cleaned blood exiting said second dialyzer.

20. A method of hemodiafiltration comprising:

supplying a blood inflow;

diafiltering said blood inflow in a first dialyzer to provide partially diafiltered blood, said first dialyzer receiving a first dialysate fluid having a first pH;

mixing said partially diafiltered blood with a substitution fluid to provide a blood/substitution fluid mixture; and diafiltering said blood/substitution fluid mixture in a second dialyzer, said second dialyzer receiving a second dialysate having a second pH, said first pH being less than said second pH.

21. A method according to claim 20, wherein said diafiltering said blood inflow comprises diffusing a portion of said blood inflow by a first countercurrent flow of said first dialysate fluid in diffusion communication with said blood inflow, and wherein said diafiltering of said blood/substitution fluid mixture comprises diffusing a portion of said blood/substitution fluid mixture by a second countercurrent flow of said second dialysate fluid in diffusion communication with said blood/substitution fluid mixture.

22. A method according to claim 20, wherein said first dialysate fluid is formed by contacting a portion of said second dialysate fluid with a pH modifying agent so that said pH of said second dialysate fluid is reduced.

23. A method according to claim 20, wherein said first pH is less than about 7.0.

24. A method according to claim 20, wherein said second pH is greater than about 7.0.

25. A method according to claim 20, wherein said first dialysate fluid is formed by:

diverting a portion of said second dialysate fluid to a container;

disposing a concentrated acid within said container so that said pH of said second dialysate fluid is reduced as said second dialysate fluid contacts said concentrated acid to form an acidic dialysate solution; and selectively mixing a predetermined amount of said acidic dialysate solution with said second dialysate fluid to form said first dialysate fluid.

26. A method according to claim 20, further comprising:

providing a mixing chamber in fluid communication with said container for receiving said acidic dialysate solution and said second dialysate outlet, said second dialysate fluid being delivered to said mixing chamber after flowing through said second dialyzer.

27. A method according to claim 26, wherein said substitution fluid has a pH substantially equal to said second pH.

* * * * *